(12) United States Patent
Math et al.

(10) Patent No.: US 12,403,149 B2
(45) Date of Patent: Sep. 2, 2025

(54) DISPERSIBLE TABLETS OF ABIRATERONE ACETATE

(71) Applicant: SHILPA MEDICARE LIMITED, Raichur (IN)

(72) Inventors: Nijaguni Revansiddayya Rudraswamy Math, Bengaluru (IN); Sreenivasa Reddy, Bengaluru (IN); Ravi Vamsi Peri, Bengaluru (IN); Shivakumar Pradeep, Bengaluru (IN)

(73) Assignee: Shilpa Medicare Limited, Karnataka (IN)

( * ) Notice: Subject to any disclaimer, the term of this patent is extended or adjusted under 35 U.S.C. 154(b) by 853 days.

(21) Appl. No.: 17/624,842

(22) PCT Filed: Jul. 2, 2020

(86) PCT No.: PCT/IB2020/056236
§ 371 (c)(1),
(2) Date: Jan. 5, 2022

(87) PCT Pub. No.: WO2021/009605
PCT Pub. Date: Jan. 21, 2021

(65) Prior Publication Data
US 2022/0257613 A1 Aug. 18, 2022

(30) Foreign Application Priority Data
Jul. 15, 2019 (IN) .............................. 201941015017

(51) Int. Cl.
*A61K 9/20* (2006.01)
*A61K 9/00* (2006.01)
*A61K 31/58* (2006.01)

(52) U.S. Cl.
CPC ............ *A61K 31/58* (2013.01); *A61K 9/0056* (2013.01)

(58) Field of Classification Search
CPC ...... A61K 9/20; A61K 9/2004; A61K 9/2013; A61K 9/2009; A61K 9/2018; A61K 9/2036; A61K 9/2054
See application file for complete search history.

(56) References Cited

U.S. PATENT DOCUMENTS

2015/0246060 A1    9/2015    Murphy et al.

FOREIGN PATENT DOCUMENTS

| WO | 2013164473 A1 | 11/2013 | |
| WO | WO-2015032873 A1 * | 3/2015 | ............. A61K 31/58 |
| WO | 2015114314 A1 | 8/2015 | |
| WO | WO-2015193380 A2 * | 12/2015 | ............. A23L 33/12 |
| WO | 2017209939 A1 | 12/2017 | |

* cited by examiner

*Primary Examiner* — Micah Paul Young

(57) ABSTRACT

The present invention relates to a dispersible tablet comprising at least 70% w/w of abiraterone acetate based on the total weight of the tablet and at least one pharmaceutically excipient selected from group consisting of diluents, binders, surfactants, glidants, disintegrants, lubricants, sweeteners and flavorants and further relates to the process for the preparation thereof.

10 Claims, No Drawings

DISPERSIBLE TABLETS OF ABIRATERONE ACETATE

FIELD OF THE INVENTION

The present invention relates to dispersible tablets comprising abiraterone acetate and the process for preparing such dispersible tablets and the use of said dispersible tablets for the treatment of prostate cancer.

BACKGROUND OF THE INVENTION

Abiraterone acetate is an inhibitor of CYP17 (17α-hydroxylase/C17,20-lyase) indicated in combination with prednisone for the treatment metastatic castration-resistant prostate cancer (CRPC) and metastatic high-risk castration-sensitive prostate cancer (CSPC). Abiraterone acetate is structurally represented as

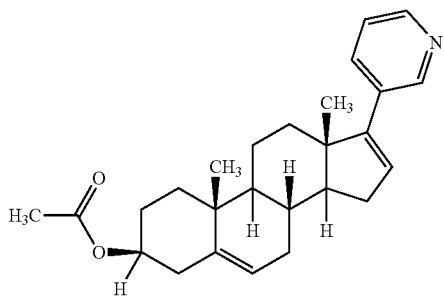

PCT Publication WO2013164473 discloses abiraterone acetate dissolved or dispersed in a carrier, wherein the carrier comprises one or more lipid excipients.

The recommended dose of abiraterone acetate is 1000 mg per day (QD) in combination with prednisone 5 mg twice a day (bid). Tablets comprising 250 mg and 500 mg abiraterone acetate are sold under the trade name Zytiga®. Thus the required dosage is comprised of four 250 mg tablets or two 500 mg tablets that have to be administered orally once a day. This situation is unsatisfactory and inconvenient to the patients to swallow four or two tablets once a day.

In order to overcome the above disadvantages, the inventors of PCT Publication WO2015114314 have developed the dispersible tablets of abiraterone acetate comprising 1000 mg of abiraterone acetate. The dispersible tablets as disclosed in example 7 of WO '314 comprises of about 50% of abiraterone acetate and require lot of other excipients which is difficult to manufacture and inconvenient for storage as it requires lot of storage space.

Therefore, there exists a need to develop the high drug load dispersible tablets comprising abiraterone which is easy to manufacture and convenient for storage.

OBJECTS OF THE INVENTION

The object of the invention is to provide a dispersible tablet comprising high drug load of abiraterone acetate.

Another object of the invention is to provide a dispersible tablet comprising abiraterone acetate for once a day administration.

Another object of the invention is to provide a dispersible tablet comprising abiraterone acetate, wherein the total daily dose is of about 1000 mg.

Another object of the present invention is to provide a process for preparing a dispersible tablet comprising of at least 70% w/w of abiraterone acetate.

SUMMARY OF THE INVENTION

The present invention provides a dispersible tablet comprising at least 70% w/w of abiraterone acetate and pharmaceutically acceptable excipients.

In one embodiment of the invention, the present invention provides a dispersible tablet comprising about 70% w/w to about 90% w/w of abiraterone acetate based on the total weight of the tablet and pharmaceutically acceptable excipients.

In another embodiment the present invention provides a dispersible tablet comprising at least 70% w/w of abiraterone acetate based on the total weight of the tablet and at least one pharmaceutically excipient selected from group consisting of diluents, binders, surfactants, glidants, disintegrants, lubricants, sweeteners and flavorants.

In further embodiment of the present invention provides a dispersible tablet comprising about 70% w/w to about 90% w/w of abiraterone acetate based on the total weight of the tablet, and at least one pharmaceutically excipient selected from group consisting of diluents, binders, surfactants, glidants, disintegrants, lubricants, sweeteners and flavorants.

In a still further embodiment, the present invention provides a dispersible tablet comprising
a) about 70% w/w to about 90% w/w of abiraterone acetate,
b) about 15% w/w to about 25% w/w of diluent,
c) about 0.2% w/w to about 2% w/w of surfactant,
d) about 0.2% w/w to about 2% w/w of glidant,
e) about 1% w/w to about 5% w/w of disintegrant
f) about 0.2% w/w to about 1% w/w of lubricant and
g) at least one excipient selected from group consisting of flavorants and sweeteners.

In a still further specific embodiment, the present invention provides a dispersible tablet consisting of
a) about 70% w/w to about 90% w/w of abiraterone acetate,
b) about 15% w/w to about 25% w/w of microcrystalline cellulose,
c) about 0.2% w/w to about 2% w/w of sodium lauryl sulfate,
d) about 0.2% w/w to about 2% w/w of colloidal silicon dioxide,
e) about 1% w/w to about 5% w/w of crospovidone,
f) about 0.2% w/w to about 1% w/w of magnesium stearate and
g) at least one excipient selected from group consisting of flavorants and sweeteners.

In another embodiment, the present invention provides a dispersible tablet comprising
a) about 70% w/w to about 90% w/w of abiraterone acetate,
b) about 15% w/w to about 25% w/w of diluent,
c) about 0.2% w/w to about 2% w/w of surfactant,
d) about 0.2% w/w to about 2% w/w of glidant,
e) about 1% w/w to about 5% w/w of disintegrant
f) about 0.2% w/w to about 1% w/w of lubricant and
g) at least one excipient selected from group consisting of flavorants and sweeteners, wherein the dispersible tablet is free of binder.

In a still further embodiment, the present invention provides a dispersible tablet consisting of a) about 70% w/w to about 90% w/w of abiraterone acetate,
b) about 15% w/w to about 25% w/w of microcrystalline cellulose,
c) about 0.2% w/w to about 2% w/w of sodium lauryl sulfate,
d) about 0.2% w/w to about 2% w/w of colloidal silicon dioxide,
e) about 1% w/w to about 5% w/w of crospovidone,
f) about 0.2% w/w to about 1% w/w of magnesium stearate and
g) at least one excipient selected from group consisting of flavorants and sweeteners, wherein the dispersible tablet is free of binder.

BRIEF DESCRIPTION OF THE INVENTION

The present invention relates to the dispersible tablets comprising of at least 70% w/w of abiraterone acetate based on the total weight of the tablet. The dispersible tablet preferably comprises about 70% w/w to about 90% w/w of abiraterone acetate and more preferably 70% w/w, 70.5% w/w, 71% w/w, 71.5% w/w, 72% w/w, 72.5% w/w, 73% w/w, 73.5% w/w, 74% w/w, 74.5% w/w, 75% w/w, 75.5% w/w, 76% w/w, 76.5% w/w, 77% w/w, 77.5% w/w, 78% w/w, 78.5% w/w, 79% w/w, 79.5% w/w, 80% w/w, 80.5% w/w, 81% w/w, 81.5% w/w, 82% w/w, 82.5% w/w, 83% w/w, 83.5% w/w, 84% w/w, 84.5% w/w, 85% w/w, 85.5% w/w, 86% w/w, 86.5% w/w, 87% w/w, 87.5% w/w, 88% w/w, 88.5% w/w, 89% w/w, 89.5% w/w and 90% w/w of abiraterone acetate based on the total weight of the tablet.

Present inventors have now surprisingly found that the formulation of abiraterone acetate in form of a dispersible tablet allows an oral dosage form with a high drug loading and which is convenient to administer to, for example elderly, and stable.

By "dispersible tablet" is meant a tablet which disperses in aqueous phase, e.g. in water, before administration.

In embodiments of the invention, the present invention provides a dispersible tablet comprising at least 70% w/w of abiraterone acetate based on the total weight of the tablet and at least one pharmaceutically excipient selected from group consisting of diluents, binders, surfactants, glidants, disintegrants, lubricants, sweeteners and flavorants.

In further embodiment of the invention, the present invention provides a dispersible tablet comprising about 70% w/w to about 90% w/w of abiraterone acetate based on the total weight of the tablet, and at least one pharmaceutically excipient selected from group consisting of diluents, binders, surfactants, glidants, disintegrants, lubricants, sweeteners and flavorants.

In embodiments of the invention, diluents used in the present invention are selected from the group consisting of lactose, microcrystalline cellulose, saccharose, sorbitol, mannitol, dextrates, dextrins, dextrose, maltodextrin and mixtures thereof. Diluent used in the dispersible tablet is of about 10% w/w to about 30% w/w based on the total weight of the dispersible tablet and more preferably of about 15% w/w to about 25% w/w based on the total weight of the dispersible tablet. The most preferably used diluent in the dispersible tablet is microcrystalline cellulose. In the present invention, the whole of diluent is included in the intra-granular portion.

In another embodiment, surfactants used in the invention are selected from the group consisting of sodium lauryl sulfate, polysorbate 80, docusate sodium or mixtures thereof. Surfactant used in the dispersible tablet is of about 0.1% w/w to about 5% w/w based on the total weight of the dispersible tablet, more preferably of about 0.2% w/w to about 1% w/w based on the total weight of the dispersible tablet. The most preferably used surfactant is sodium lauryl sulfate. In the present invention, the whole of surfactant is included in the intra-granular portion.

In embodiments of the invention, glidants used in the invention are selected from the group consisting of colloidal silicon dioxide, talc or mixtures thereof. Glidant used in the dispersible tablet is of about 0.1% w/w to about 5% w/w based on the total weight of the dispersible tablet and more preferably of about 0.2% w/w to about 2% w/w based on the total weight of the dispersible tablet. The most preferably used glidant is colloidal silicon dioxide. In the present invention, the whole of glidant is included in the intra-granular portion.

In further embodiment, disintegrants used in the invention are selected from the group consisting of crospovidone, pre-gelatinized starch and croscarmellose sodium or mixtures thereof. Disintegrant used in the dispersible tablet is of about 0.5% w/w to about 10% w/w based on the total weight of the dispersible tablet, more preferably of about 1% w/w to about 5% w/w based on the total weight of the dispersible tablet. The most preferably used disintegrant is crospovidone. In the present invention, the whole of disintegrant is included in the intra-granular portion.

In further embodiments of the invention, lubricants used in the invention are selected from the group consisting of magnesium stearate, sodium stearyl fumarate or mixtures thereof. Lubricants used in the dispersible tablet is of about 0.1% w/w to about 1.5% w/w based on the total weight of the dispersible tablet and more preferably of about 0.2% w/w to about 1% w/w based on the total weight of the dispersible tablet. The most preferably used lubricant is magnesium stearate. Lubricant is included in both the intra-granular and extra-granular portion.

In another embodiment, binders used in the invention are selected from the group consisting of polyvinyl pyrrolidone (also known as povidone), copovidone, polyethylene glycol (s), acacia, alginic acid, agar, calcium carragenan, cellulose derivatives such as ethyl cellulose, methyl cellulose, hydroxypropyl cellulose, hydroxypropyl methyl cellulose, sodium carboxymethylcellulose, dextrin, gelatin, gum arabic, guar gum, tragacanth, sodium alginate, or mixtures thereof. Binder used in the dispersible tablet is of about 0.5% w/w to about 5% w/w based on the total weight of the dispersible tablet.

In another embodiment of the invention, the sweeteners used in the present invention are selected from aspartame, sucralose, dextrose, fructose, ammonium glycyrrhizinate, maltose, mannitol, sorbitol and xylitol and/or combinations thereof. Sweeteners used in the dispersible tablet is of about 0.5% w/w to about 5% w/w based on the total weight of the dispersible tablet. The most preferably used sweetener is aspartame.

Flavoring agents used in the present invention are selected from Examples of the flavour agents are selected from the group consisting of peppermint flavour, cooling flavour (menthol), flavour oils, flavouring aromatic oil, peppermint oil, clove oil, bay oil, anise oil, eucalyptus oil thyme oil, oil of bitter almonds. Flavouring agents include, vanilla, chocolate flavour, citrus oils, fruit essences like Orange, strawberry, banana, and any combinations thereof. Flavoring agents used in the dispersible tablet is of 0.2% w/w to about 5% w/w based on the total weight of the dispersible tablet In a still further embodiment, the present invention provides a dispersible tablet comprising a) about 70% w/w to about 90% w/w of abiraterone acetate,
b) about 15% w/w to about 25% w/w of diluent,
c) about 0.2% w/w to about 2% w/w of surfactant,
d) about 0.2% w/w to about 2% w/w of glidant,
e) about 1% w/w to about 5% w/w of disintegrant
f) about 0.2% w/w to about 1% w/w of lubricant and
g) at least one excipient selected from group consisting of flavorants and sweeteners.

In a still further specific embodiment, the present invention provides a dispersible tablet consisting of
a) about 70% w/w to about 90% w/w of abiraterone acetate,
b) about 15% w/w to about 25% w/w of microcrystalline cellulose,
c) about 0.2% w/w to about 2% w/w of sodium lauryl sulfate,
d) about 0.2% w/w to about 2% w/w of colloidal silicon dioxide,
e) about 1% w/w to about 5% w/w of crospovidone,
f) about 0.2% w/w to about 1% w/w of magnesium stearate and
g) at least one excipient selected from group consisting of flavorants and sweeteners.

In another embodiment, the present invention provides a dispersible tablet comprising
a) about 70% w/w to about 90% w/w of abiraterone acetate,
b) about 15% w/w to about 25% w/w of diluent,
c) about 0.2% w/w to about 2% w/w of surfactant,
d) about 0.2% w/w to about 2% w/w of glidant,
e) about 1% w/w to about 5% w/w of disintegrant
f) about 0.2% w/w to about 1% w/w of lubricant and
g) at least one excipient selected from group consisting of flavorants and sweeteners, wherein the dispersible tablet is free of binder.

In a still further embodiment, the present invention provides a dispersible tablet consisting of
a) about 70% w/w to about 90% w/w of abiraterone acetate,
b) about 15% w/w to about 25% w/w of microcrystalline cellulose,
c) about 0.2% w/w to about 2% w/w of sodium lauryl sulfate,
d) about 0.2% w/w to about 2% w/w of colloidal silicon dioxide,
e) about 1% w/w to about 5% w/w of crospovidone,
f) about 0.2% w/w to about 1% w/w of magnesium stearate and
g) at least one excipient selected from group consisting of flavorants and sweeteners, wherein the dispersible tablet is free of binder.

In another embodiment, the present invention provides a dispersible tablet consisting of
a) about 70% w/w to about 90% w/w of abiraterone acetate,
b) about 15% w/w to about 25% w/w of microcrystalline cellulose,
c) about 0.2% w/w to about 2% w/w of sodium lauryl sulfate,
d) about 0.2% w/w to about 2% w/w of colloidal silicon dioxide,
e) about 1% w/w to about 5% w/w of crospovidone,
f) about 0.2% w/w to about 1% w/w of magnesium stearate and
g) at least one excipient selected from group consisting of flavorants and sweeteners,
wherein whole of microcrystalline cellulose, sodium lauryl sulfate, colloidal silicon dioxide, crospovidone are present intragranular-portion,
wherein about 43% w/w of the magnesium stearate based on the total weight of the magnesium stearate is present in the intragranular-portion and about 57% w/w of the magnesium stearate based on the total weight of the magnesium stearate is present in the extragranular-portion and,
wherein whole of the flavorants and sweeteners are present in the extragranular portion.

In a further embodiment, the present invention provides a dispersible tablet consisting of
a) about 70% w/w to about 90% w/w of abiraterone acetate,
b) about 15% w/w to about 25% w/w of microcrystalline cellulose,
c) about 0.2% w/w to about 2% w/w of sodium lauryl sulfate,
d) about 0.2% w/w to about 2% w/w of colloidal silicon dioxide,
e) about 1% w/w to about 5% w/w of crospovidone,
f) about 0.2% w/w to about 1% w/w of magnesium stearate and
g) at least one excipient selected from group consisting of flavorants and sweeteners,
wherein whole of microcrystalline cellulose, sodium lauryl sulfate, colloidal silicon dioxide, crospovidone are present intragranular-portion, wherein about 43% w/w of the magnesium stearate based on the total weight of the magnesium stearate is present in the intragranular-portion and,
about 57% w/w of the magnesium stearate based on the total weight of the magnesium stearate is present in the extragranular-portion,
wherein whole of the flavorants and sweeteners are present in the extragranular portion and
wherein the dispersible tablet is free of binder.

In another embodiment, the present invention provides a process for the preparation of dispersible tablet, wherein the process comprises the steps of
a) mixing the abiraterone acetate and pharmaceutically acceptable excipients;
b) wet-granulation;
c) mixing with pharmaceutically acceptable excipients to form a mixture; and
d) compressing the mixture obtained in step (c) to form a dispersible tablet.

In a further embodiment, the present invention provides a process for the preparation of dispersible tablet, wherein the process comprises the steps of
a) mixing the abiraterone acetate and pharmaceutically acceptable excipients;
b) dry-granulation;
c) mixing with pharmaceutically acceptable excipients to form a mixture; and
d) compressing the mixture obtained in step (c) to form a dispersible tablet.

In another embodiment, the present invention provides a process for the preparation of dispersible tablet, wherein the process comprises the steps of
a) mixing the abiraterone acetate, diluents, surfactants, glidants, disintegrants and about 43% w/w of the lubricant based on the total weight of the lubricant;

b) dry granulating by roll-compaction;
c) mixing about 57% w/w of the lubricant based on the total weight of the lubricant, flavorants and sweeteners to form a mixture; and
d) compressing the mixture obtained in step (c) to form a dispersible tablet.

In a still further embodiment, the present invention provides a process for the preparation of dispersible tablet, wherein the process comprises the steps of
a) mixing the abiraterone acetate, microcrystalline cellulose, sodium lauryl sulfate, colloidal silicon dioxide, crospovidone and about 43% w/w of the magnesium stearate based on the total weight of the magnesium stearate;
b) dry granulating by roll-compaction;
c) mixing about 57% w/w of the magnesium stearate based on the total weight of the magnesium stearate, flavorants and sweeteners to form a mixture; and
d) compressing the mixture obtained in step (c) to form a dispersible tablet.

The present inventors have surprisingly found that the fast disintegration property of less than 2 minutes of the present dispersible tablets is achieved using purified water at 15° C. to 25° C. (Ph. Eur Disintegration test) when the dispersible tablet is prepared without using binder (the dispersible tablet is free of binder) and stored at 40° C./75% RH for a period of 1 Month.

The following example is provided to illustrate the present invention. It is understood, however, that the invention is not limited to the specific conditions or details described in the example below. The example should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Example 1

Composition

| S. No | Ingredients | Quantity Mg/Tab |
|---|---|---|
| | Dry Mix | |
| 1. | Abiraterone acetate | 1000 |
| 2. | Mannitol | 64 |
| 3. | Croscarmellose sodium | 20 |
| 4. | Colloidal silicon dioxide | 6 |
| | Binder Solution | |
| 5. | Povidone K 30 | 34 |
| 6. | Sodium Lauryl sulfate | 5 |
| 7. | Purified water | q.s |
| | Blending & Lubrication | |
| 8. | Crospovidone | 30 |
| 9. | Colloidal silicon dioxide | 4 |
| 10. | Pre-gelatinized starch | 30 |
| 11. | Magnesium Stearate | 7 |
| | Total Tablet weight | 1200 |

Process for Preparation

A) Dry Mix: Abiraterone Acetate, mannitol, croscarmellose sodium and colloidal silicon dioxide were mixed in a granulator.
B) Preparation of Binder solution: PVP K30 and sodium lauryl sulfate was dissolved in water to form the binder solution.
C) Granulation: The mixture obtained in step (A) was granulated with the binder solution obtained in step (B).
D) Blending & Lubrication: The granules obtained in step (C) were dried, blended and lubricated with crospovidone, colloidal silicon dioxide, pre-gelatinised starch and magnesium stearate.
E) Compression: The lubricated granules obtained in step (D) were compressed to form dispersible tablets.

Example 2

Composition

| S. No | Ingredients | Quantity Mg/Tab |
|---|---|---|
| | Intra-granular portion | |
| 1. | Abiraterone acetate | 1000 |
| 2. | Microcrystalline cellulose | 163 |
| 3. | Sodium lauryl sulfate | 13 |
| 4. | Colloidal Silicon dioxide | 20 |
| 5. | Crospovidone | 40 |
| 6. | Aspartame | 20 |
| 7. | Orange flavor | 14 |
| | Extra-granular portion | |
| 8. | Crospovidone | 10 |
| 9. | Copovidone | 10 |
| 10. | Stearic acid | 4 |
| 11. | Magnesium Stearate | 4 |
| 12. | Orange flavor | 2 |
| | Total Tablet weight | 1300 |

Process for Preparation

A) Sifting: Sift abiraterone acetate, microcrystalline cellulose, sodium lauryl sulfate, colloidal silicon dioxide, crospovidone aspartame, orange flavor.
B) Roll Compaction: Compact the materials of step A and mill the compacted flakes.
C) Sifting: Sift extragranular materials of crospovidone, copovidone, stearic acid and orange flavor.
D) Blending: The granules obtained in Step (B) were blended with Step (C).
E) Sifting: Sift extragranular material of magnesium stearate separately.
F) Lubrication: Lubricate blend of step (D) with step (E).
G) Compression: The lubricant granules obtained in step (F) were compressed to form dispersible tablets.

Example 3

Composition

| S. No | Ingredients | Quantity Mg/Tab |
|---|---|---|
| | Intra-granular portion | |
| 1. | Abiraterone acetate | 1000 |
| 2. | Microcrystalline cellulose | 250 |
| 3. | Sodium lauryl sulfate | 13 |

-continued

| S. No | Ingredients | Quantity Mg/Tab |
|---|---|---|
| 4. | Colloidal Silicon dioxide | 20 |
| 5. | Crospovidone | 30 |
| 6. | Magnesium Stearate | 3 |
| | Extra-granular portion | |
| 7. | Magnesium Stearate | 4 |
| 8. | Orange flavor | 10 |
| 9. | Aspartame | 20 |
| | Total Tablet weight | 1350 |

Process for Preparation

A) Sifting: Sift abiraterone acetate, microcrystalline cellulose, sodium lauryl sulfate, crospovidone, colloidal silicon dioxide and magnesium stearate
B) Roll Compaction: Compact the material of Step A and mill the compacted flakes.
C) Sifting: Sift extragranular materials of aspartame and orange flavor.
D) Blending: The granules obtained step (B) were blended with step (C).
E) Sifting: Sift extragranular material of magnesium stearate.
F) Lubrication: Lubricate blend of step (D) with step (E).
G) Compression: The lubricated granules obtained in step (F) were compressed to form dispersible tablets.

Example 4: Disintegration Testing

Disintegrating testing of dispersible tablets of example 2 and 3 are carried out in using purified water at 15° C. to 25° C. (Ph. Eur Disintegration test) at the initial condition and the after one month stored at 40° C./75% RH and the results are tabulated in Table 1.

TABLE 1

| | Example | |
|---|---|---|
| | Example 2 | Example 3 |
| Disintegration time (Initial) | 1 minute 3 seconds | 1 min 24 seconds |
| Disintegration time (40° C./75% RH) 1 Month | 8 minute 20 seconds | 1 minute 31 seconds |

It is observed that the example 3 without the binder has the less disintegration time of less than 2 minutes in accelerated condition (40° C./75% RH) after one month.

We claim:
1. A dispersible tablet comprising at least 70% w/w of abiraterone acetate and pharmaceutically acceptable excipients, wherein the dispersible tablet is free of binder.
2. The dispersible tablet as claimed in claim 1 comprising about 70% w/w to about 90% w/w of abiraterone acetate based on the total weight of the dispersible tablet.
3. The dispersible tablet as claimed in claim 1 comprising the pharmaceutically acceptable excipients selected from the group consisting of diluents, surfactants, glidants, disintegrants, lubricants, sweeteners and flavorants.
4. The dispersible tablet as claimed in claim 1, wherein diluents are selected from group consisting of lactose, microcrystalline cellulose, saccharose, sorbitol, mannitol, dextrates, dextrins, dextrose and maltodextrin.
5. The dispersible tablet as claimed in claim 1, wherein surfactants are selected from the group consisting of sodium lauryl sulfate, polysorbate 80, and docusate sodium.
6. The dispersible tablet as claimed in claim 1, wherein glidants are selected from group consisting of colloidal silicon dioxide and talc.
7. The dispersible tablet as claimed in claim 1, wherein disintegrants are selected from group consisting of crospovidone, pre-gelatinized starch and croscarmellose sodium.
8. The dispersible tablet as claimed in claim 1, wherein lubricants are selected from group consisting of magnesium stearate and sodium stearyl fumarate.
9. A dispersible tablet as claimed in claim 1 comprising
   a) about 70% w/w to about 90% w/w of abiraterone acetate,
   b) about 15% w/w to about 25% w/w of diluent,
   c) about 0.2% w/w to about 2% w/w of surfactant,
   d) about 0.2% w/w to about 2% w/w of glidant,
   e) about 1% w/w to about 5% w/w of disintegrant
   f) about 0.2% w/w to about 1% w/w of lubricant and
   g) at least one excipient selected from group consisting of flavorants and sweeteners.
10. A dispersible tablet consisting of
   a) about 70% w/w to about 90% w/w of abiraterone acetate,
   b) about 15% w/w to about 25% w/w of microcrystalline cellulose,
   c) about 0.2% w/w to about 2% w/w of sodium lauryl sulfate,
   d) about 0.2% w/w to about 2% w/w of colloidal silicon dioxide,
   e) about 1% w/w to about 5% w/w of crospovidone,
   f) about 0.2% w/w to about 1% w/w of magnesium stearate and
   g) at least one excipient selected from group consisting of flavorants and sweeteners,
   wherein the dispersible tablet is free of binder.

* * * * *